US011142615B2

(12) United States Patent
Sohn et al.

(10) Patent No.: US 11,142,615 B2
(45) Date of Patent: Oct. 12, 2021

(54) SUPER ABSORBENT POLYMER AND METHOD FOR PREPARING SAME

(71) Applicant: LG Chem, Ltd., Seoul (KR)

(72) Inventors: Jung Min Sohn, Daejeon (KR); Soo Jin Lee, Daejeon (KR)

(73) Assignee: LG Chem, Ltd.

( * ) Notice: Subject to any disclaimer, the term of this patent is extended or adjusted under 35 U.S.C. 154(b) by 252 days.

(21) Appl. No.: 16/340,891

(22) PCT Filed: Oct. 16, 2018

(86) PCT No.: PCT/KR2018/012193
§ 371 (c)(1),
(2) Date: Apr. 10, 2019

(87) PCT Pub. No.: WO2019/093670
PCT Pub. Date: May 16, 2019

(65) Prior Publication Data
US 2020/0223991 A1 Jul. 16, 2020

(30) Foreign Application Priority Data
Nov. 7, 2017 (KR) .......................... 10-2017-0147584

(51) Int. Cl.
| | | |
|---|---|---|
| *C08J 3/24* | (2006.01) | |
| *A61L 15/24* | (2006.01) | |
| *A61L 15/60* | (2006.01) | |
| *C08F 220/06* | (2006.01) | |
| *C08J 3/075* | (2006.01) | |
| *C08J 3/12* | (2006.01) | |

(52) U.S. Cl.
CPC .............. *C08J 3/245* (2013.01); *A61L 15/24* (2013.01); *A61L 15/60* (2013.01); *C08F 220/06* (2013.01); *C08J 3/075* (2013.01); *C08J 3/12* (2013.01); *C08J 2333/02* (2013.01)

(58) Field of Classification Search
CPC .. A61L 15/24; A61L 15/60; C08F 2/10; C08F 6/008; C08F 220/06; C08J 3/00; C08J 3/075; C08J 3/12; C08J 3/24; C08J 2333/02; C08J 2333/08; C08J 2333/10
See application file for complete search history.

(56) References Cited

U.S. PATENT DOCUMENTS

| | | | |
|---|---|---|---|
| 5,409,771 A | 4/1995 | Dahmen et al. | |
| 5,422,405 A | 6/1995 | Dairoku et al. | |
| 5,610,208 A * | 3/1997 | Dairoku | A61L 15/24 525/384 |
| 6,444,744 B1 * | 9/2002 | Fujimaru | A61L 15/24 524/556 |
| 6,562,879 B1 * | 5/2003 | Hatsuda | C08J 3/12 241/24.28 |
| 2014/0031473 A1 * | 1/2014 | Nogi | C08J 3/12 524/320 |
| 2014/0042364 A1 | 2/2014 | Nogi et al. | |
| 2015/0093575 A1 | 4/2015 | Naumann et al. | |
| 2015/0315321 A1 * | 11/2015 | Won | C08J 3/245 525/328.8 |
| 2016/0151531 A1 | 6/2016 | Lee et al. | |
| 2016/0375171 A1 | 12/2016 | Omori et al. | |
| 2017/0009026 A1 | 1/2017 | Nam et al. | |
| 2018/0304232 A1 | 10/2018 | Nam et al. | |
| 2018/0312680 A1 | 11/2018 | Seo et al. | |
| 2019/0099739 A1 | 4/2019 | Lee et al. | |

FOREIGN PATENT DOCUMENTS

| | | | | |
|---|---|---|---|---|
| CN | 105392805 | A | 3/2016 | |
| CN | 106414527 | A | 2/2017 | |
| EP | 0536128 | A1 | 4/1993 | |
| EP | 0605150 | A1 | 7/1994 | |
| EP | 2669318 | A1 * | 12/2013 | ................ C08J 3/24 |
| EP | 2669318 | A1 | 12/2013 | |
| EP | 2881419 | A1 * | 6/2015 | ............ C08L 101/14 |

(Continued)

OTHER PUBLICATIONS

Belmares, et al. "Hildebrand and Hans Solubility Parameters from Molecular Dynamics with Applications to Electronic Nose Polymer Sensors", J Comput Chem, 25 (15), 1814-1826, Nov. 2004. (Year: 2004).*
Hansen, "Hansen Solubility Parameters: A User's Handbook" CRC Press, 2007. (Year: 2007).*
Steven Abbott, HSP Basics, www.stevenabbott.co.uk/practical-solubility/hsp-basics.php, accessed Feb. 18, 2021. (Year: 2021).*
Buchholz, "Chemistry of Superabsorbent Polyacrylates", Modern Superabsorbent Polymer Technology, 1998, pp. 19-67, John Wiley & Sons, USA.
Third Party Observation for Application No. EP18857397.6 dated Mar. 6, 2020, 17 pages.
Third Party Observation for Application No. PCT/KR2018/012193 submitted on Feb. 28, 2020, 10 pages.

(Continued)

*Primary Examiner* — Christopher M Rodd
(74) *Attorney, Agent, or Firm* — Lerner, David, Littenberg, Krumholz & Mentlik, LLP

(57) ABSTRACT

The present invention relates to a super absorbent polymer which not only has excellent basic absorption performance but also can improve rewet characteristics and leakage suppression characteristics of hygienic materials such as diapers, and a method for preparing the same. The super absorbent polymer includes: a base polymer powder including a first cross-linked polymer of a water-soluble ethylenically unsaturated monomer having an acidic group of which at least a part is neutralized; and a surface crosslinked layer that is formed on the base polymer powder and includes a second cross-linked polymer in which the first crosslinked polymer is further crosslinked via a surface crosslinking agent, wherein the surface crosslinking agent includes a mixture of plural kinds of cyclic alkylene carbonates, and where the mixture has a Hansen solubility parameter by hydrogen bonding component of 13 or more.

11 Claims, No Drawings

(56) References Cited

FOREIGN PATENT DOCUMENTS

| EP | 2881419 | A1 | 6/2015 |
|---|---|---|---|
| EP | 3424988 | A1 | 1/2019 |
| JP | H05508425 | A | 11/1993 |
| JP | H06184320 | A | 7/1994 |
| JP | H08057310 | A | 3/1996 |
| JP | 2015120933 | A | 7/2015 |
| JP | 2016112474 | A | 6/2016 |
| JP | 2016516877 | A | 6/2016 |
| KR | 20140102264 | A | 8/2014 |
| KR | 20150020030 | A | 2/2015 |
| KR | 20150088219 | A | 7/2015 |
| KR | 20160102217 | A | 8/2016 |
| KR | 20170098196 | A | 8/2017 |
| KR | 20170106157 | A | 9/2017 |
| WO | 2006033477 | A1 | 3/2006 |
| WO | 2017142204 | A1 | 8/2017 |
| WO | 2018117390 | A1 | 6/2018 |

OTHER PUBLICATIONS

Extended European Search Report including the Written Opinion for Application No. EP 18857397.6 dated Dec. 16, 2019, 13 pages.

Sonnati et al., "Glycerol Carbonate as a Versatile Building Block for Tomorrow: Synthesis, Reactivity, Properties and Applications," Journal of the Royal Society of Chemmistry, Green Chemistry, vol. 15, No. 2, Jan. 1, 2013 (Jan. 1, 2013), pp. 283-306.

Steven Abbott, "Hansen Solubility Parameter Calculations," Feb. 1, 2015 (Feb. 1, 2015), XP055649826, Retrieved from the Internet: URL:https://www.turi.org/content/download/9584/166492/file/Hansen%20Solubility%20Parameters.%20Calculations.%20February%202015.pdf [retrieved on Dec. 5, 2019].

Odian, George, "Principles of Polymerization." Second Edition, 1981, John Wiley & Sons, Inc., p. 203.

Schwalm, Reinhold, "UV Coatings Basics Recent Developments and New Applications", Elsevier Science, Dec. 21, 2006, p. 115.

Hansen, Charles M., "Hansen Solubility Parameters: A User's Handbook, Second Edition," CRC Press, Taylor & Francis Group, © 2007, 22 pages. ISBN: 0849372488.

International Search Report for PCT/KR2018/012193 dated Jan. 30, 2019.

Chernyak Y. Dielectric constant, dipole moment, and solubility parameters of some cyclic acid esters. Journal of Chemical & Engineering Data. Mar. 9, 2006;51(2):416-8.

Search Report from Office Action for Chinese Application No. 201880004067.9 dated Jun. 2, 2021; 2 pages.

* cited by examiner

SUPER ABSORBENT POLYMER AND METHOD FOR PREPARING SAME

CROSS-REFERENCE TO RELATED APPLICATION(S)

This application is a national phase entry under 35 U.S.C. § 371 of International Application No. PCT/KR2018/012193, filed Oct. 16, 2018, which claims priority to Korean Patent Application No. 10-2017-0147584, filed Nov. 7, 2017, the disclosures of which are incorporated herein by reference.

TECHNICAL FIELD

The present invention relates to a super absorbent polymer which not only has excellent basic absorption performance but also can improve rewet characteristics and leakage suppression characteristics of hygienic materials such as diapers, and a method for preparing the same.

BACKGROUND

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. For these applications, it is necessary to exhibit a high moisture absorbency against moisture, and also it is necessary to exhibit excellent absorbency under pressure or the like that does not release the absorbed water even in the external pressure.

In addition, when the super absorbent polymer is included in hygienic materials such as diapers, it is necessary to maximally widely diffuse urine and the like. Thereby, it is possible to further improve the absorption performance and absorption rate of hygienic materials by wholly utilizing super absorbent polymer particles contained in the entire area of the hygienic material absorption layer. Further, due to such spreading characteristics, it is possible to further improve the rewet characteristic of diaper which prevents urine and the like once absorbed by the super absorbent resin from again causing leakage or oozing. In addition, it is possible to improve the leakage suppression characteristic of diaper.

Previously, attempts have been made to improve the characteristics of widely diffusing urine and the like by changing the design of hygienic materials such as diapers. For example, attempts have been made to improve the spreading characteristics of urine and the like by a method of introducing an acquisition distribution layer (ADL) or the like into hygienic materials, or by a method of utilizing an absorption channel.

However, the improvement of the spreading characteristic due to design changes of hygienic materials themselves was not sufficient, and additional improvements thereon have been continuously requested.

Technical Problem

The present invention provides a super absorbent polymer which not only has excellent basic absorption performance but also can improve rewet characteristics and leakage suppression characteristics of hygienic materials by widely diffusing urine and like due to characteristic improvement of hygienic materials themselves, and a method for preparing the same.

Technical Solution

The present invention provides a super absorbent polymer comprising:

a base polymer powder including a first cross-linked polymer of a water-soluble ethylenically unsaturated monomer having an acidic group of which at least a part is neutralized; and a surface crosslinked layer that is formed on the base polymer powder and includes a second cross-linked polymer in which the first crosslinked polymer is further crosslinked via a surface crosslinking agent, wherein the surface crosslinking agent includes a mixture of plural kinds of cyclic alkylene carbonates, and where the mixture has a Hansen solubility parameter by hydrogen bonding component of 13 or more.

The present invention also provides a method for preparing a super absorbent polymer comprising the steps of:

performing a crosslinking polymerization of a water-soluble ethylenically unsaturated monomer having an acidic group of which at least a part is neutralized in the presence of an internal crosslinking agent to form a hydrogel polymer containing a first crosslinked polymer;

drying, pulverizing, and classifying the crosslinked hydrogel polymer to form a base polymer powder; and surface-crosslinking the base polymer powder by heat treatment in the presence of a surface cross-linking agent, wherein the surface crosslinking agent includes a mixture of plural kinds of cyclic alkylene carbonates, and wherein the mixture has a Hansen solubility parameter by hydrogen bonding component of 13 or more.

Hereinafter, a super absorbent polymer according to specific embodiments of the present invention and a preparation method thereof will be described in more detail. However, this is merely presented as an example of the present invention, and will be apparent to those skilled in the art that the scope of the present invention is not limited to these embodiments, and various modifications can be made to the embodiments within the scope of the present invention.

In addition, unless stated otherwise throughout this specification, the term "comprises" or "contains" refers to including any constituent element (or constituent component) without particular limitation, and it cannot be interpreted as a meaning of excluding an addition of other constituent element (or constituent component).

According to one embodiment of the invention, there is provided a super absorbent polymer comprising:

a base polymer powder including a first cross-linked polymer of a water-soluble ethylenically unsaturated monomer having an acidic group of which at least a part is neutralized; and a surface crosslinked layer that is formed on the base polymer powder and includes a second cross-linked polymer in which the first crosslinked polymer is further crosslinked via a surface crosslinking agent, wherein the surface crosslinking agent includes a mixture of plural kinds of cyclic alkylene carbonates, and where the mixture has a Hansen solubility parameter by hydrogen bonding component of 13 or more.

As a result of further experiments by the present inventors, it has been found that, as the surface crosslinking proceeds using a mixture having a Hansen solubility parameter by hydrogen bonding component of 13 or more as a mixture containing a specific surface crosslinking agent mixture, i.e., a mixture containing plural kinds of cyclic alkylene carbonates, the super absorbent polymer itself can quickly and widely diffuse urine absorbed in the hygienic materials to improve the rewet characteristic and leakage suppression characteristic of hygienic materials while excellently maintaining the basic absorption performance of the super absorbent polymer.

This is presumably because plural kinds of cyclic alkylene carbonates can synergize with each other by the following principle. In order for the Hansen solubility parameter by hydrogen bonding component of the mixture to be 13 or more, a second cyclic alkylene carbonate such as glycerol carbonate in which the Hansen solubility parameter by hydrogen bonding component is 15 or more, or 16 or more, can be used together with a first cyclic alkylene carbonate such as ethylene carbonate or propylene carbonate, which has been widely used as a surface crosslinking agent for a long time.

First, it is known that the first cyclic alkylene carbonate such as ethylene carbonate or propylene carbonate has excellent surface crosslinking properties, and by using this, it is possible to excellently exhibit the basic performance (for example, high absorbency under pressure, or liquid permeability, etc.) of the super absorbent polymer. Further, the second cyclic alkylene carbonate having a higher Hansen solubility parameter by hydrogen bonding component can impart hydrophilicity to the surface of the super absorbent polymer particles, thereby allowing the urine and the like absorbed in the hygienic materials to be diffused quickly and widely along the surface of the super absorbent polymer particles. As a result, the super absorbent polymer of one embodiment not only exhibits excellent basic absorption performance and liquid permeability, but also can widely diffuse urine and the like absorbed in the hygienic materials to improve rewet characteristics and leakage suppression properties of the hygienic materials.

Hereinafter, the super absorbent polymer of one embodiment will be described in more detail.

The term "super absorbent polymer" refers to a super absorbent polymer comprising: a base polymer powder including a first cross-linked polymer of a water-soluble ethylenically unsaturated monomer having an acidic group of which at least a part is neutralized; and a surface cross-linked layer that is formed on the base polymer powder and includes a second cross-linked polymer in which the first crosslinked polymer is further crosslinked via a surface crosslinking agent.

The water-soluble ethylenically unsaturated monomer may be any monomer commonly used for the preparation of a super absorbent polymer. As a non-limiting example, the water-soluble ethylenically unsaturated monomer may be a compound represented by the following Chemical Formula 1:

  [Chemical Formula 1]

in Chemical Formula 1, $R_1$ is an alkyl group having 2 to 5 carbon atoms containing an unsaturated bond, $M^1$ is a hydrogen atom, a monovalent or divalent metal, an ammonium group or an organic amine salt.

Suitably, the monomer may be one or more selected from the group consisting of acrylic acid, methacrylic acid, and monovalent metal salts, divalent metal salts, ammonium salts, and organic amine salts of these acids.

When a (meth)acrylic acid and/or a salt thereof is used as the water-soluble ethylenically unsaturated monomer in this way, it is advantageous in that a super absorbent polymer having improved water absorptivity can be obtained. In addition, as the monomer, an anionic monomer such as maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methylpropane sulfonic acid, and a salt thereof; a non-ionic hydrophilic group-containing monomer such as (meth)acrylamide, N-substituted (meth) acrylate, 2-hydroxyethyl(meth)acrylate, 2-hydroxypropyl (meth)acrylate, methoxypolyethyleneglycol(meth)acrylate, or polyethyleneglycol(meth)acrylate; and an amino group-containing unsaturated monomer such as (N,N)-dimethylaminoethyl(meth)acrylate, or (N,N)-dimethylaminopropyl (meth)acrylamide, and a quaternary compound thereof may be used.

Here, the water-soluble ethylenically unsaturated monomers may have an acidic group, in which at least a part of the acidic group may be neutralized. Preferably, those in which the monomer is partially neutralized with an alkaline substance such as sodium hydroxide, potassium hydroxide, ammonium hydroxide or the like can be used.

In this case, a degree of neutralization of the monomer may be 40 to 95 mol %, or 40 to 80 mol %, or 45 to 75 mol %. The range of the degree of neutralization may vary depending on the final physical properties. An excessively high degree of neutralization causes the neutralized monomers to be precipitated, and thus polymerization may not readily occur, whereas an excessively low degree of neutralization not only greatly deteriorates the absorbency of the polymer, but also endows the polymer with hard-to-handle properties, like elastic rubber.

In the super absorbent polymer of one embodiment, the "first crosslinked polymer" means that the above-mentioned water-soluble ethylene-based unsaturated monomer is polymerized in the presence of an internal crosslinking agent, and the "base polymer powder" means a substance containing such a first crosslinked polymer. In addition, the "second crosslinked polymer" means a substance in which the first crosslinked polymer is further crosslinked via a surface crosslinking agent, whereby the surface crosslinked layer including the same is formed on the base polymer powder.

In the super absorbent polymer of one embodiment, the first crosslinked polymer contained in the base polymer powder may be a polymer in which the monomer is subjected to a crosslinking polymerization in the presence of at least one internal crosslinking agent selected from the group consisting of a bis(meth)acrylamide having 8 to 12 carbon atoms, a poly(meth)acrylates of polyols having 2 to 10 carbon atoms and a poly (meth) allyl ether of polyol having 2 to 10 carbon atoms. More specific examples of the internal crosslinking agent include, but are not limited to, trimethylolpropane tri(meth)acrylate, ethylene glycol di(meth)acrylate, polyethylene glycol di(meth)acrylate, propylene glycol di(meth)acrylate, polypropylene glycol di(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, and the like. In addition, various internal crosslinking agents known to be usable for the production of the super absorbent polymer can be used without particular limitation.

Further, in the super absorbent polymer of one embodiment, the second crosslinked polymer contained in the surface crosslinked layer may be a polymer in which the aforementioned first crosslinked polymer is further crosslinked via a specific internal crosslinking agent. In particular, in the super absorbent polymer of one embodiment, a surface crosslinking agent including a mixture of plural kinds of cyclic alkylene carbonates is used to form the second crosslinked polymer and the surface crosslinked layer.

At this time, the surface crosslinking agent in the mixture state may exhibit a characteristic that a Hansen solubility parameter by hydrogen bonding component is 13 or more, or 14 to 18, or 14.5 to 16.0.

The Hansen solubility parameter for the aforementioned mixture and the cyclic alkylene carbonate contained therein can be confirmed and calculated according to the method described in C. M. Hansen, "Hansen Solubility Parameters; A User's Handbook", CRC Press, 2nd ed. (2012). More specifically, according to the aforementioned literature, the Hansen solubility parameter of a component can be divided into three components corresponding to a dispersion force, a polar force, and a hydrogen bonding component, respectively. The super absorbent polymer of one embodiment defines surface crosslinking agents through the Hansen solubility parameter by hydrogen bonding component among these three Hansen solubility parameters.

That is, the Hansen solubility parameter by hydrogen-bonding component of each cyclic alkylene carbonate is calculated and confirmed according to the method described in the aforementioned literature, and then the Hansen solubility parameter value by hydrogen bonding component of the surface crosslinking agent in the mixture state can be determined by the weight average value of the parameter value of each cyclic alkylene carbonate based on the content (wt. %) contained in the mixture.

These parameter values can define the hydrophilic range of the surface crosslinking agent in the mixture state. According to the experimental results of the present inventors, as the surface crosslinking agent in the mixture state has a Hansen solubility parameter by hydrogen bonding component of 13 or more, the super absorbent polymer of one embodiment has excellent absorption performance and liquid permeability, and also appropriate hydrophilicity is imparted to the surface of the super absorbent polymer particles (for example, the surface of the surface crosslinked layer), and thus, urine and the like absorbed in the hygiene materials can be diffused quickly and widely along the surface of the super absorbent polymer particles. As a result, the rewet characteristic and the leakage suppression characteristic for the hygiene materials such as diapers can be greatly improved.

On the other hand, in order for the surface crosslinking agent including the mixture of the plural kinds of cyclic alkylene carbonates to have a Hansen solubility parameter by a hydrogen bonding component of 13 or more, the surface crosslinking agent may include both a first cyclic alkylene carbonate having a Hansen solubility parameter by hydrogen bonding component of 10 to 13, and a second cyclic alkylene carbonate having a Hansen solubility parameter by hydrogen bonding component of 16 to 20.

Among them, the first cyclic alkylene carbonate can ensure the basic absorption performance and/or liquid permeability of the super absorbent polymer, and specific examples thereof include ethylene carbonate and propylene carbonate. In addition, the second cyclic alkylene carbonate is a component for imparting hydrophilicity to the surface of the super absorbent polymer particles to improve the rewet characteristic and the leakage suppression characteristic of the hygiene materials, and specific examples thereof include glycerol carbonate and the like.

These first and second cyclic alkylene carbonates may be included in a weight ratio of 0.9:1 to 1:2 in the surface crosslinking agent, and thereby, the super absorbent polymer of one embodiment not only exhibits more excellent absorption performance and/or liquid permeability, but also can further improve the rewet characteristic and the leakage suppression characteristic of the hygiene materials.

On the other hand, the super absorbent polymer of the embodiment described above may have a particle size of 150 to 850 μm. More specifically, at least 95% by weight of the base polymer powder and the super absorbent polymer containing the same may have a particle size of 150 to 850 μm, and a fine powder having a particle size of less than 150 μm may be less than 3% by weight.

In addition, the super absorbent polymer of the one embodiment is excellent in basic absorbency under no pressure and liquid permeability, and this can be defined by physical properties such as CRC and GBP.

Specifically, the super absorbent polymer of one embodiment may have a centrifuge retention capacity (CRC) for a physiological saline solution (0.9 wt % sodium chloride aqueous solution) for 30 minutes of 27 to 37 g/g, or 28 to 32 g/g. Such a centrifuge retention capacity (CRC) range can define an excellent absorbency under no pressure exhibited by the super absorbent polymer of one embodiment.

The centrifuge retention capacity (CRC) for a physiological saline solution can be calculated according to the following Calculation Equation 1 after absorbing the super absorbent polymer in a physiological saline solution for 30 minutes:

$$CRC(g/g) = \{[W_2(g) - W_1(g) - W_0(g)]/W_0(g)\} \quad \text{[Calculation Equation 1]}$$

in Calculation Equation 1, $W_0(g)$ is an initial weight(g) of the super absorbent polymer, $W_1(g)$ is a weight of bag measured after impregnating a nonwoven fabric bag not containing a super absorbent polymer in a physiological saline solution at room temperature for 30 minutes and then dehydrating the same by using a centrifuge at 250 G for 3 minutes, and $W_2(g)$ is a weight of bag measured after impregnating a nonwoven fabric bag containing a super absorbent polymer in physiological saline at room temperature for 30 minutes and then dehydrating the same by using a centrifuge at 250 G for 3 minutes.

Further, the super absorbent polymer of one embodiment may have a gel bed permeability (GBP) for a physiological saline solution of 23 darcy or more, or 23 to 35 darcy, or 26 to 32 darcy. This can define excellent liquid permeability of the super absorbent polymer of one embodiment.

The gel bed permeability (GBP) for a physiological saline solution can be measured in units of Darcy or cm$^2$ according to the following method described in Korean Patent Application No. 10-2014-7018005. One Darcy means that it permits a flow of 1 mm/s of a fluid with viscosity of 1 cP under a pressure gradient of 1 atm/cm acting across an area of 1 cm$^2$. Gel bed permeability has the same unit as area, and 1 darcy is the same as $0.98692 \times 10^{-12}$ m$^2$ or $0.98692 \times 10^{-8}$ cm$^3$. More specifically, as used herein, GBP means a penetration (or permeability) of a swollen gel layer (or bed) under conditions referred to as 0 psi free swell state (a Gel Bed Permeability (GBP) Under 0 psi Swell Pressure Test). The GBP can be measured using the apparatus shown in FIGS of Korean Patent Application No. 10-2014-7018005.

On the other hand, in the super absorbent polymer of one embodiment, appropriate hydrophilicity is imparted to its surface, and urine and the like absorbed in the hygiene materials can be diffused rapidly and widely along the surface of the super absorbent polymer particles. As a result, the rewet characteristic and the leakage suppression characteristic of the hygiene materials such as diapers can be greatly improved. Such spreading characteristics of urine and the like can be confirmed by the spreading characteristic of Examples described later. This spreading characteristic can be calculated by measuring with the maximum length (mm) at which the physiological saline solution is diffused in the super absorbent polymer, when uniformly spreading 1 g of the super absorbent polymer so as to have a constant thickness and width to a length of 200 mm, injecting 2 g of a 0.9 wt % physiological saline solution mixed with a dye into the center of the place where the super absorbent polymer is diffused, and then absorbing it. The super absorbent polymer of one embodiment may have a spreading characteristic of 140 to 200 mm, or 145 to 180 mm, and thereby, the rewet characteristic of the hygiene materials can be greatly improved.

On the other hand, a super absorbent polymer satisfying all the various physical properties of the above-described embodiment can be prepared by a preparation method including obtaining a hydrogel polymer by crosslinking polymerization, then, drying, pulverizing and classifying the hydrogel polymer to form a base polymer powder, and performing a surface crosslinking step in the presence of a specific surface crosslinking agent.

According to another embodiment of the present invention, there is provided a method for preparing the above-mentioned super absorbent polymer. This preparation method may include the steps of: performing a crosslinking polymerization of a water-soluble ethylenically unsaturated monomer having an acidic group of which at least a part is neutralized in the presence of an internal crosslinking agent to form a hydrogel polymer containing a first crosslinked polymer; drying, pulverizing, and classifying the crosslinked hydrogel polymer to form a base polymer powder; and surface-crosslinking the base polymer powder by heat treatment in the presence of a surface crosslinking agent, wherein the surface crosslinking agent includes a mixture of plural kinds of cyclic alkylene carbonates, and wherein the mixture has a Hansen solubility parameter by hydrogen bonding component of 13 or more.

Hereinafter, the preparation method will be described in detail for each step.

First, the preparation method of another embodiment includes forming a hydrogel polymer by crosslinking polymerization. Specifically, it is a step of thermally polymerizing or photo-polymerizing a monomer composition containing a water-soluble ethylenically unsaturated monomer and a polymerization initiator in the presence of an internal crosslinking agent to form a hydrogel polymer.

The water-soluble ethylenically unsaturated monomer contained in the monomer composition is as described above.

In addition, the monomer composition may include a polymerization initiator generally used in the preparation of the superabsorbent polymer. As a non-limiting example, the polymerization initiator may be a thermal polymerization initiator or a photo-polymerization initiator, depending on a polymerization method. However, even though the photo-polymerization is performed, a certain amount of heat may be generated by UV irradiation, etc., and also generated with exothermic polymerization reaction. Therefore, the thermal polymerization initiator may be further included.

As the photo-polymerization initiator, for example, one or more compounds selected from the group consisting of benzoin ether, dialkyl acetophenone, hydroxyl alkylketone, phenyl glyoxylate, benzyl dimethyl ketal, acyl phosphine, and alpha-aminoketone may be used. Among them, as the specific example of acyl phosphine, commercially available Lucirin TPO, namely, 2,4,6-trimethyl-benzoyl-trimethyl phosphine oxide may be used. More various photo-polymerization initiators are well disclosed in "UV Coatings: Basics, Recent Developments and New Application (Elsevier, 2007)" written by Reinhold Schwalm, p 115, which may be incorporated herein by reference.

As the thermal polymerization initiator, one or more compounds selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4$)$_2S_2O_8$), and the like. Further, examples of the azo-based initiator may include 2,2-azobis-(2-amidinopropane)dihydrochloride, 2,2-azobis-(N,N-dimethylene)isobutyramidine dihydrochloride, 2-(carbamoylazo)isobutylonitrile, 2,2-azobis[2-(2-imidazolin-2-yl)propane]dihydrochloride, 4,4-azobis-(4-cyanovaleric acid) and the like. More various thermal polymerization initiators are well disclosed in "Principle of Polymerization" written by Odian, (Wiley, 1981), p 203, which may be incorporated herein by reference.

Such polymerization initiator may be added at a concentration of about 0.001 to 1% by weight with respect to the monomer composition. That is, if the concentration of the polymerization initiator is too low, the polymerization rate becomes low and thus a large amount of residual monomers may be extracted from the final product, which is not preferable. On the contrary, if the concentration of the polymerization initiator is too high, a polymer chain making up a network may become short, and thus, the physical properties of polymer may be degraded such as increase in the content of water-soluble components and decrease in absorbency under pressure, which is not preferable.

Meanwhile, the monomer composition includes a crosslinking agent ("internal crosslinking agent") for improving the physical properties of polymer by the polymerization of the water-soluble ethylenically unsaturated monomer. The initiators are intended to internally cross-link hydrogel polymer, and can be used separately from the "surface crosslinking agent" described later.

In particular, in the preparation method of another embodiment described above, the above-mentioned internal crosslinking agent, for example, a bis(meth)acrylamide having 8 to 12 carbon atoms, a poly(meth)acrylate of polyol having 2 to 10 carbon atoms or a poly(meth)allyl ether of polyol having 2 to 10 carbon atoms, etc. may be used. Thereby, a hydrogel polymer to which internal crosslinking is suitably applied can be obtained. However, since the kind of the internal crosslinking agent has already been described above, a further description thereof will be omitted.

Further, the internal crosslinking agent may be used in an amount of 0.4 to 2 parts by weight, or 0.4 to 1.8 parts by weight based on 100 parts by weight of the monomer composition including the internal crosslinking agent, the monomer and the like. Thereby, the degree of internal crosslinking of the hydrogel polymer and the base polymer powder can be controlled, and the absorption performance, liquid permeability, etc. of the super absorbent polymer can be optimized. However, if the content of the internal crosslinking agent is excessively large, the basic absorption performance of the super absorbent polymer may be lowered.

In addition, the monomer composition may further contain additives such as a thickener, a plasticizer, a preservation stabilizer, and an antioxidant, if necessary.

Further, the monomer composition may be prepared in the form of a solution in which the raw materials such as the above-mentioned monomers, polymerization initiator and internal crosslinking agent are dissolved in a solvent.

In this case, as the usable solvent, any solvent may be used without limitations in the constitution, as long as it is able to dissolve the above raw materials. Example of the solvent that can be used include water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof.

The formation of hydrogel polymer through polymerization of the monomer composition can be carried out by a conventional polymerization method, and the process is not particularly limited. As a non-limiting example, the polymerization process may be largely classified into a thermal polymerization and a photo-polymerization depending on a polymerization energy source. The thermal polymerization may be performed in a reactor like a kneader equipped with agitating spindles, and the photo-polymerization can be carried out in a reactor equipped with a movable conveyor belt.

As an example, the monomer composition is injected into a reactor like a kneader equipped with the agitating spindles, and thermal polymerization is performed by providing hot air thereto or heating the reactor, to thereby obtain the hydrogel polymer. In this case, the hydrogel polymer, which is discharged from the outlet of the reactor according to the type of agitating spindles equipped in the reactor, can be obtained into a particle having several millimeters to several centimeters. Specifically, the resulting hydrogel polymer may be obtained in various forms according to the concentration of the monomer mixture injected thereto, the injection speed, or the like, and a hydrogel polymer having a (weight average) particle size of 2 to 50 mm may be generally obtained.

As another example, when the photo-polymerization of the monomer composition is carried out in a reactor equipped with a movable conveyor belt, the hydrogel polymer may be obtained in the form of a sheet. In this case, the thickness of the sheet may vary according to the concentration of the monomer composition injected thereto and the injection speed. Usually, the sheet is preferably controlled to have a thickness of 0.5 cm to 10 cm in order to uniformly polymerize the entire sheet and also secure production speed.

The hydrogel polymer obtained by the above-mentioned method may have a water content of 40 to 80% by weight. Meanwhile, the "water content" as used herein means a weight occupied by moisture with respect to a total amount of the hydrogel polymer, which may be the value obtained by subtracting the weight of the dried polymer from the weight of the hydrogel polymer. Specifically, the water content is defined as a value calculated by measuring the weight loss due to evaporation of water in the polymer during the drying process of increasing the temperature of the polymer with infrared heating. At this time, the water content is measured under the drying conditions determined as follows: the drying temperature is increased from room temperature to about 180° C., and then the temperature is maintained at 180° C., and the total drying time is set as 20 minutes, including 5 minutes for the temperature rising step.

Next, the step of drying the obtained hydrogel polymer is carried out. If necessary, the step of coarsely pulverizing the hydrogel polymer before drying may be further carried out in order to increase the efficiency of the drying step.

A pulverizing device used herein is not limited by its configuration, and specific examples thereof may include any one selected from the group consisting of a vertical pulverizer, a turbo cutter, a turbo grinder, a rotary cutter mill, a cutter mill, a disc mill, a shred crusher, a crusher, a chopper, and a disc cutter. However, it is not limited to the above-described examples.

In this case, the coarsely pulverizing step may be performed such that the hydrogel polymer has a particle size of about 2 mm to 10 mm. To pulverize the polymer to have a particle size of less than 2 mm is technically not easy due to high water content of the hydrogel polymer, and a phenomenon of agglomeration between the pulverized particles may occur. Meanwhile, if the polymer is pulverized to have a particle size of larger than 10 mm, the effect of increasing the efficiency in the subsequent drying step may be poor.

The hydrogel polymer coarsely pulverized as above or immediately after polymerization without the coarsely pulverizing step is subjected to a drying step. At this time, a drying temperature of the drying step may be 150 to 250° C. When the drying temperature is lower than 150° C., there is a concern that the drying time becomes excessively long or the physical properties of the super absorbent polymer finally formed may be deteriorated, and when the drying temperature is higher than 250° C., only the surface of the polymer is excessively dried, and thus there is a concern that fine powder may be generated during the subsequent pulverization step and the physical properties of the super absorbent polymer finally formed may be deteriorated. Therefore, the drying process may be preferably performed at a temperature of 150 to 200° C., and more preferably 170 to 195° C.

Meanwhile, the drying may be carried out for 20 to 90 minutes, in consideration of the process efficiency, but is not limited thereto.

The drying method may be selected and used in the drying step without limitation in the constitution as long as it may be generally used in the process of drying the hydrogel polymer. Specifically, the drying step may be carried out by a method of supplying hot air, irradiating infrared rays, irradiating microwaves, irradiating ultraviolet rays, or the like. When the drying step as above is finished, the water content of the polymer may be about 0.1 to about 10% by weight.

Next, the dried polymer obtained from the drying step is subjected to a pulverization step.

The polymer powder obtained from the pulverization step may have a particle size of 150 to 850 μm. Specific examples of a pulverizing device that may be used to achieve the above particle size may include a pin mill, a hammer mill, a screw mill, a roll mill, a disc mill, a jog mill, or the like, but are not limited thereto.

In order to manage the physical properties of the super absorbent polymer powder finally produced after the pulverization step, a separate classifying step may be performed according to the particle size of the polymer powder obtained after pulverization. Preferably, a polymer having a particle size of 150 to 850 μm is classified and only particles having such particle size are subjected to the surface crosslinking reaction, and finally, is commercialized. The particle size distribution of the base polymer powder obtained through such process has already been described above, and thus more specific description thereof will be omitted.

On the other hand, after the base polymer powder is produced through the classification step described above, the base polymer powder can be subjected to heat treatment and surface crosslinking in the presence of a surface crosslinking agent to form super absorbent polymer particles. The surface crosslinking induces a crosslinking reaction on the surface of the base polymer powder in the presence of a surface crosslinking agent. Through such surface crosslinking, a surface crosslinked layer is formed on the surface of the base polymer powder.

More specifically, in the preparation method of another embodiment described above, the surface crosslinking agent including a mixture of plural kinds of cyclic alkylene carbonates and having a Hansen solubility parameter by hydrogen bonding component of 13 or more is used, and since the kind of the surface crosslinking agent has already been fully described, additional explanation will be omitted.

In the surface crosslinking step using the surface crosslinking agent, the content of the surface crosslinking agent may be appropriately controlled according to the kind of crosslinking agent, reaction conditions, etc., and may be preferably adjusted to 0.001 to 5 parts by weight based on 100 parts by weight of the base polymer powder. If the content of the surface crosslinking agent is excessively low, the surface modification may not be properly performed, and the physical properties of the final polymer may be deteriorated. Conversely, if an excess amount of the surface crosslinking agent is used, the basic absorption capacity of the polymer may rather decrease due to excessive surface crosslinking reaction, which is not preferable.

On the other hand, the surface crosslinking agent is added to the base polymer powder in the form of a surface crosslinking solution containing the surface crosslinking agent. The method of adding the surface crosslinking agent is not particularly limited by its configuration. For example, a method of placing the surface crosslinking solution and the base polymer powder into a reaction tank and mixing them, a method of spraying a surface crosslinking solution onto the base polymer powder, a method in which the base polymer powder and the surface crosslinking solution are continuously supplied in a continuously operating mixer and mixed, or the like can be used.

In addition, the surface crosslinking liquid may further include water and/or a hydrophilic organic solvent as a medium. Thus, there is an advantage that the surface crosslinking agent and the like can be evenly dispersed on the base polymer powder. In this case, the content of water and the hydrophilic inorganic solvent can be applied by adjusting the addition ratio with respect to 100 parts by weight of the base polymer powder, for the purpose of inducing the uniform dissolution/dispersion of the surface crosslinking agent, preventing the phenomenon of aggregation of the base polymer powder and at the same time optimizing the surface penetration depth of the surface crosslinking agent.

The surface crosslinking reaction can be proceeded by heating the surface crosslinking solution-added base polymer powder at a maximum reaction temperature of 140 to 200° C., or 170 to 195° C. for 5 minutes to 60 minutes, or 10 minutes to 50 minutes, or 20 minutes to 45 minutes. More specifically, the surface crosslinking step can be proceeded by subjecting to a heat treatment under the conditions in which the temperature is raised from an initial temperature of 20° C. to 130° C. or 40° C. to 120° C. to the maximum reaction temperature over a period of 10 minutes or more, or 10 minutes to 30 minutes, and the maximum temperature is maintained for 5 minutes to 60 minutes.

By satisfying the conditions of such a surface crosslinking step (in particular, the temperature raising conditions and the reaction conditions at the maximum temperature of the reaction), the super absorbent polymer suitably satisfying the physical properties such as excellent liquid permeability can be prepared.

A means for raising the temperature for surface crosslinking reaction is not particularly limited. Heating may be performed by providing a heating medium or by directly providing a heat source. The type of the heating medium applicable herein may be a hot fluid such as steam, hot air, hot oil, or the like, but is not limited thereto. Further, the temperature of the heating medium provided may be properly controlled, considering the means of the heating medium, the temperature-raising rate, and the temperature-raising target temperature. Meanwhile, as the heat source provided directly, an electric heater or a gas heater may be used, but is not limited to the above-described examples.

The super absorbent polymer obtained according to the above-mentioned preparation method can widely diffuse urine and the like absorbed in the hygiene materials while excellently maintaining absorption performance such as a centrifuge retention capacity and liquid permeability.

Advantageous Effects

The super absorbent polymer according to the present invention can allow urine and the like absorbed in the hygiene materials to rapidly and widely diffuse along the surface of the super absorbent polymer particles, while excellently maintaining the basic absorption performance, liquid permeability and the like. As a result, the super absorbent polymer of the present invention can improve the rewet characteristic, leakage suppression characteristic and the like of the hygienic materials.

DETAILED DESCRIPTION OF THE EMBODIMENTS

Hereinafter, preferred examples are provided for better understanding of the invention. However, these Examples are given for illustrative purposes only and are not intended to limit the scope of the present invention thereto.

Example 1

500 g of acrylic acid and 3 g of polyethylene glycol diacrylate (Mw=523) were added and mixed. Then, 0.01 g of diphenyl(2,4,6-trimethylbenzoyl)-phosphine oxide was added and dissolved. Then, 896.4 g of 24.5 wt % sodium hydroxide aqueous solution was added, and nitrogen was continuously added to prepare a water-soluble unsaturated monomer aqueous solution. Then, the temperature of the aqueous solution was cooled to 50° C., and the aqueous solution was irradiated with ultraviolet rays for 90 seconds to obtain a hydrogel-like polymer. The obtained hydrogel polymer was pulverized using a pulverizing device. Classification was carried out with a standard mesh sieve according to ASTM Standard to prepare a base polymer powder having a particle size of 150 to 850 μm.

Subsequently, with respect to 100 parts by weight of the prepared base polymer powder, 1 part by weight of glycerol carbonate (Hansen solubility parameter by hydrogen bonding component: 18.9), 1 part by weight of propylene carbonate (Hansen solubility parameter by hydrogen bonding component: 10.8) and 4 parts by weight of water were mixed to prepare a surface crosslinking solution. Based on the respective solubility parameters of the glycerol carbonate and propylene carbonate in such a surface crosslinking solution, the Hansen solubility parameter by hydrogen bonding component of the surface crosslinking agent in the mixture state calculated by the weight average value thereof was calculated to be 14.85. For reference, the solubility parameter is a value measured a weight average value only for a mixture of glycerol carbonate and propylene carbonate except water in the surface crosslinked solution.

Subsequently, the surface crosslinking solution was sprayed onto the base polymer powder, stirred at room temperature and mixed so that the surface crosslinking solution was evenly distributed on the base polymer powder. Then, the base polymer powder mixed with the surface crosslinking solution was put into the surface crosslinking reactor and the surface crosslinking reaction was carried out. In the surface crosslinking reactor, it was confirmed that the base polymer powder was gradually heated at an initial temperature near 80° C. After 30 minutes elapsed, operation was performed so as to reach the maximum reaction temperature of 190° C. After reaching the maximum reaction temperature, additional reaction was carried out for 30 minutes, and a sample of the finally produced super absorbent polymer was taken. After the surface crosslinking step, classification was carried out with a standard mesh sieve according to ASTM Standard to prepare a super absorbent polymer of Example 1 having a particle size of 150 μm to 850 μm.

Example 2

The base polymer powder was prepared in the same manner as in Example 1.

In the preparation of the surface crosslinking solution, with respect to 100 parts by weight of the base polymer powder, 1.5 part by weight of glycerol carbonate (Hansen solubility parameter by hydrogen bonding component: 18.9), 0.9 part by weight of propylene carbonate (Hansen solubility parameter by hydrogen bonding component: 10.8) and 4 parts by weight of water were mixed to prepare a surface crosslinking solution. Based on the respective solubility parameters of the glycerol carbonate and propylene carbonate in such a surface crosslinking solution, the Hansen solubility parameter by hydrogen bonding component of the surface crosslinking agent in the mixture state calculated by the weight average value thereof was calculated to be 15.86. For reference, the solubility parameter is a value measured a weight average value only for a mixture of glycerol carbonate and propylene carbonate except water in the surface crosslinked solution.

Subsequently, surface crosslinking and the like proceeded in the same manner as in Example 1 to prepare a super absorbent resin of Example 2 having a particle size of 150 μm to 850 μm.

Example 3

The base polymer powder was prepared in the same manner as in Example 1.

In the preparation of the surface crosslinking solution, with respect to 100 parts by weight of the base polymer powder, 1 part by weight of glycerol carbonate (Hansen solubility parameter by hydrogen bonding component: 18.9), 1 part by weight of ethylene carbonate (Hansen solubility parameter by hydrogen bonding component: 12.3) and 4 parts by weight of water were mixed to prepare a surface crosslinking solution. Based on the respective solubility parameters of the glycerol carbonate and ethylene carbonate in such a surface crosslinking solution, the Hansen solubility parameter by hydrogen bonding component of the surface crosslinking agent in the mixture state calculated by the weight average value thereof was calculated to be 15.6. For reference, the solubility parameter is a value measured a weight average value only for a mixture of glycerol carbonate and ethylene carbonate except water in the surface crosslinked solution.

Subsequently, surface crosslinking and the like proceeded in the same manner as in Example 1 to prepare a super absorbent resin of Example 3 having a particle size of 150 μm to 850 μm.

Example 4

The base polymer powder was prepared in the same manner as in Example 1.

In the preparation of the surface crosslinking solution, with respect to 100 parts by weight of the base polymer powder, 1 part by weight of glycerol carbonate (Hansen solubility parameter by hydrogen bonding component: 18.9), 0.5 part by weight of ethylene carbonate (Hansen solubility parameter by hydrogen bonding component: 12.3) and 4 parts by weight of water were mixed to prepare a surface crosslinking solution. Based on the respective solubility parameters of the glycerol carbonate and ethylene carbonate in such a surface crosslinking solution, the Hansen solubility parameter by hydrogen bonding component of the surface crosslinking agent in the mixture state calculated by the weight average value thereof was calculated to be 16.7. For reference, the solubility parameter is a value measured a weight average value only for a mixture of glycerol carbonate and ethylene carbonate except water in the surface crosslinked solution.

Subsequently, surface crosslinking and the like proceeded in the same manner as in Example 1 to prepare a super absorbent resin of Example 4 having a particle size of 150 μm to 850 μm.

Comparative Example 1

The base polymer powder was prepared in the same manner as in Example 1.

In the preparation of the surface crosslinking solution, with respect to 100 parts by weight of the base polymer powder, 1.0 part by weight of ethylene carbonate (Hansen solubility parameter by hydrogen bonding component:

12.3), 1.0 part by weight of propylene carbonate (Hansen solubility parameter by hydrogen bonding component: 10.8) and 4 parts by weight of water were mixed to prepare a surface crosslinking solution. Based on the respective solubility parameters of the ethylene carbonate and propylene carbonate in such a surface crosslinking solution, the Hansen solubility parameter by hydrogen bonding component of the surface crosslinking agent in the mixture state calculated by the weight average value thereof was calculated to be 11.55. For reference, the solubility parameter is a value measured a weight average value only for a mixture of ethylene carbonate and propylene carbonate except water in the surface crosslinked solution.

Subsequently, surface crosslinking and the like proceeded in the same manner as in Example 1 to prepare a super absorbent resin of Comparative Example 1 having a particle size of 150 μm to 850 μm.

Comparative Example 2

The base polymer powder was prepared in the same manner as in Example 1.

In the preparation of the surface crosslinking solution, with respect to 100 parts by weight of the base polymer powder, 1.0 part by weight of ethylene carbonate (Hansen solubility parameter by hydrogen bonding component: 12.3) and 4 parts by weight of water were mixed to prepare a surface crosslinking solution. Based on the respective solubility parameters of the ethylene carbonate in such a surface crosslinking solution, the Hansen solubility parameter by hydrogen bonding component of the surface crosslinking agent calculated by the weight average value thereof was calculated to be 12.3. For reference, the solubility parameter is a value measured a weight average value only for ethylene carbonate except water in the surface crosslinked solution.

Subsequently, surface crosslinking and the like proceeded in the same manner as in Example 1 to prepare a super absorbent resin of Comparative Example 2 having a particle size of 150 μm to 850 μm.

Comparative Example 3

The base polymer powder was prepared in the same manner as in Example 1.

In the preparation of the surface crosslinking solution, with respect to 100 parts by weight of the base polymer powder, 1.5 part by weight of glycerol carbonate (Hansen solubility parameter by hydrogen bonding component: 18.9) and 4 parts by weight of water were mixed to prepare a surface crosslinking solution. Based on the respective solubility parameters of the glycerol carbonate in such a surface crosslinking solution, the Hansen solubility parameter by hydrogen bonding component of the surface crosslinking agent calculated by the weight average value thereof was calculated to be 18.9. For reference, the solubility parameter is a value measured a weight average value only for glycerol carbonate except water in the surface crosslinked solution.

Subsequently, surface crosslinking and the like proceeded in the same manner as in Example 1 to prepare a super absorbent resin of Comparative Example 3 having a particle size of 150 μm to 850 μm.

Comparative Example 4

The base polymer powder was prepared in the same manner as in Example 1.

In the preparation of the surface crosslinking solution, with respect to 100 parts by weight of the base polymer powder, 1.5 part by weight of propylene carbonate (Hansen solubility parameter by hydrogen bonding component: 10.8) and 4 parts by weight of water were mixed to prepare a surface crosslinking solution. Based on the respective solubility parameters of the propylene carbonate in such a surface crosslinking solution, the Hansen solubility parameter by hydrogen bonding component of the surface crosslinking agent calculated by the weight average value thereof was calculated to be 10.8. For reference, the solubility parameter is a value measured a weight average value only for propylene carbonate except water in the surface crosslinked solution.

Subsequently, surface crosslinking and the like proceeded in the same manner as in Example 1 to prepare a super absorbent resin of Comparative Example 4 having a particle size of 150 μm to 850 μm.

Experimental Example

The physical properties of each super absorbent polymer prepared in Examples and Comparative Examples were measured and evaluated by the following methods.

(1) Particle Size

The particle sizes of the base polymer powders and the super absorbent polymers used in Examples and Comparative Examples were measured according to EDANA (European Disposables and Nonwovens Association) recommended test method No. WSP 220.3.

(2) Centrifuge Retention Capacity (CRC)

The centrifuge retention capacity (CRC) by water absorption capacity under a non-loading condition was measured in accordance with EDANA (European Disposables and Nonwovens Association) recommended test method No. WSP 241.3. $W_0$ (g, about 0.2 g) of the super absorbent polymers were uniformly put in a nonwoven fabric-made bag, followed by sealing. Then, the bag was immersed in a physiological saline solution composed of 0.9 wt % aqueous sodium chloride solution at room temperature. After 30 minutes, water was removed from the bag by centrifugation at 250 G for 3 minutes, and the weight $W_2(g)$ of the bag was then measured. Further, the same procedure was carried out without using the super absorbent polymer, and then the resultant weight $W_1(g)$ was measured. Using the respective weights thus obtained, CRC (g/g) was calculated according to the following Calculation Equation 1, thereby confirming the centrifuge retention capacity.

$$CRC(g/g) = \{[W_2(g) - W_1(g) - W_0(g)]/W_0(g)\} \quad \text{[Calculation Equation 1]}$$

(3) Gel Bed Permeability (GBP)

Free swell gel bed permeability (GBP) in a physiological saline solution was measured according to the following method described in Korean Patent Application. No. 10-2014-7018005.

In detail, an apparatus illustrated in FIGS of Korean Patent Application. No. 10-2014-7018005 was used to conduct a free swell GBP test. First, a plunger with a weight seated thereon was placed in an empty sample container, and the height from the top of the weight to the bottom of the sample container was measured using a suitable gauge accurate to 0.01 mm. The force the thickness gauge applies during measurement was controlled to less than about 0.74 N.

Meanwhile, among the super absorbent polymers to be tested for GBP, super absorbent polymers, which were passed through a US standard 30 mesh screen and retained on a US standard 50 mesh screen, were selected to obtain the super absorbent polymer having a particle size of 300 μm to 600 μm.

About 2.0 g of the super absorbent polymer thus classified was placed in a sample container and spread out evenly on the bottom of the sample container. This container without the plunger and weight therein was then submerged in a 0.9% by weight physiological saline solution for about 60 min to allow the super absorbent polymer to swell free of any restraining load. At this time, the sample container was set on a mesh located in a liquid reservoir such that the sample container was raised slightly above the bottom of the liquid reservoir. The mesh did not inhibit the flow of the physiological saline solution into the sample container. During saturation, a depth of the physiological saline solution was controlled such that the surface within the sample container was defined solely by the swollen super absorbent polymer, rather than the physiological saline solution.

At the end of this period, the plunger and weight assembly was placed on the swollen super absorbent polymer in the sample container and then the sample container, plunger, weight, and then swollen super absorbent polymer were removed from the solution. Then, before GBP measurement, the sample container, plunger, weight, and swollen super absorbent polymer were allowed to remain at rest for about 30 seconds on a large grid non-deformable plate of uniform thickness. The height from the top of the weight to the bottom of the sample container was measured again by using the same thickness gauge that was used previously. The height measurement of the apparatus where the plunger and the weight were placed in the empty sample container was subtracted from the height measurement of the apparatus containing the swollen superabsorbent polymer to obtain the thickness or height "H" of the swollen super absorbent polymer.

For GBP measurement, a flow of 0.9% physiological saline solution was delivered into the sample container with the swollen super absorbent polymer, the plunger, and the weight inside. The flow rate of the physiological saline solution into the container was adjusted to cause the physiological saline solution to overflow the top of the cylinder, resulting in a consistent head pressure equal to the height of the sample container. The quantity of solution passing through the swollen super absorbent polymer versus time was measured gravimetrically using a scale and a beaker. Data points from the scale were collected every second for at least 60 seconds once the overflow began. The flow rate (Q) through the swollen super absorbent polymer was determined in units of g/sec by a linear least-squares fit of fluid (g) passing through the swollen super absorbent polymer versus time (sec).

GBP (cm$^2$) was calculated from the obtained data according to the following Calculation Equation 2.

$$K=[Q \times H \times \mu]/[A \times \rho \times P] \quad \text{[Calculation Equation 2]}$$

in Calculation Equation 2, K is gel bed permeability (cm$^2$), Q is a flow rate (g/sec), H is a height of swollen super absorbent polymer (cm), μ is liquid viscosity (P) (about 1 cp for the physiological saline solution used in this test), A is a cross-sectional area for liquid flow (28.27 cm$^2$ for the sample container used in this test), ρ is a liquid density (g/cm$^3$) (about 1 g/cm$^3$ for the physiological solution used in this test), and P is a hydrostatic pressure (dyne/cm$^2$) (normally about 7,797 dyne/cm$^2$). The hydrostatic pressure is calculated from $P=\rho \times g \times h$, wherein ρ is a liquid density (g/cm$^3$), g is gravitational acceleration (nominally 981 cm/sec$^2$), and h is a fluid height (e.g., 7.95 cm for the GBP test described herein).

At least two samples were tested, and an average of the results was determined as free swell GBP of the super absorbent polymer, and the unit was converted to Darcys (1 Darcy=$0.98692 \times 10^{-8}$ cm$^2$).

(4) Spreading Characteristic (mm)

1 g of the super absorbent polymer of Examples and Comparative Examples was uniformly spread over a length of 200 mm so as to have a constant thickness and width, and 2 g of a 0.9 wt % physiological saline solution mixed with a dye was injected into the center of the place where the super absorbent polymer was spread and then absorbed. Then, the spreading characteristic was calculated by measuring with the maximum length (mm) at which the physiological saline solution was diffused in the super absorbent polymer.

The physical properties of Examples 1 to 4 and Comparative Examples 1 to 4 measured by the above method are summarized in Table 1 below.

TABLE 1

| Unit | CRC g/g | GBP darcy | Spreading mm |
| --- | --- | --- | --- |
| Example 1 | 28.0 | 28 | 150 |
| Example 2 | 29.5 | 26 | 170 |
| Example 3 | 29 | 25 | 161 |
| Example 4 | 29.3 | 29 | 172 |
| Comparative Example 1 | 29.6 | 14 | 125 |
| Comparative Example 2 | 30.4 | 19 | 110 |
| Comparative Example 3 | 29.7 | 12 | 135 |
| Comparative Example 4 | 30.1 | 5 | 105 |

Referring to Table 1 above, it was confirmed that Examples 1 to 4 exhibited the basic absorption performance (CRC) equal to or higher than that of Comparative Examples 1 to 4, and also had remarkably excellent liquid permeability (GBP) and the spreading characteristic as compared with Comparative Example, thereby widely diffusing urine and the like.

The invention claimed is:

1. A super absorbent polymer comprising:
   a base polymer powder including a first cross-linked polymer of a water-soluble ethylenically unsaturated monomer having an acidic group of which at least a part is neutralized; and
   a surface crosslinked layer that is present on the base polymer powder and includes a second cross-linked polymer in which the first crosslinked polymer is further crosslinked via a surface crosslinking agent,
   wherein the surface crosslinking agent includes a mixture of plural kinds of cyclic alkylene carbonates, and
   wherein the mixture includes a first cyclic alkylene carbonate of ethylene carbonate or propylene carbonate, and a second cyclic alkylene carbonate of glycerol carbonate.

2. The super absorbent polymer according to claim 1, wherein the first and second cyclic alkylene carbonates included in a weight ratio of 0.9:1 to 1:2.

3. The super absorbent polymer according to claim 1, wherein the super absorbent polymer exhibits a centrifuge retention capacity (CRC) of 27 to 37 g/g, and a gel bed permeability (GBP) of 23 to 35 darcy.

4. A method for preparing a super absorbent polymer of claim 1, comprising:
performing a crosslinking polymerization of a water-soluble ethylenically unsaturated monomer having an acidic group of which at least a part is neutralized in the presence of an internal crosslinking agent to form a hydrogel polymer containing a first crosslinked polymer;
drying, pulverizing, and classifying the crosslinked hydrogel polymer to form a base polymer powder; and
surface-crosslinking the base polymer powder by heat treatment in the presence of a surface cross-linking agent,
wherein the surface crosslinking agent includes a mixture of plural kinds of cyclic alkylene carbonates, and
wherein the mixture includes a first cyclic alkylene carbonate of ethylene carbonate or propylene carbonate, and a second cyclic alkylene carbonate of glycerol carbonate.

5. The method according to claim 4, wherein the water-soluble ethylenically unsaturated monomer includes an anionic monomer; a non-ionic, hydrophilic group-containing monomer or an amino group-containing unsaturated monomer.

6. The method according to claim 4, wherein the internal crosslinking agent includes a bis(meth)acrylamide having 8 to 12 carbon atoms, a poly(meth)acrylates of polyols having 2 to 10 carbon atoms or a poly (meth)allyl ether of polyol having 2 to 10 carbon atoms.

7. The method according to claim 4, wherein the base polymer powder is pulverized and classified such that the base polymer powder has a particle size of 150 to 850 µm.

8. The method according to claim 4, wherein the surface crosslinking step is performed by heat treatment by raising an initial temperature of 20° C. to 130° C. to a maximum temperature of 140° C. to 200° C. in 10 min to 30 min and maintaining the maximum temperature for 5 min to 60 min.

9. The method according to claim 5, wherein the anionic monomer includes acrylic acid, methacrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methylpropane sulfonic acid, or a salt thereof.

10. The method according to claim 5, wherein the non-ionic, hydrophilic group-containing monomer includes (meth)acrylamide, N-substituted (meth)acrylate, 2-hydroxyethyl(meth)acrylate, 2-hydroxypropyl(meth)acrylate, methoxypolyethylene glycol(meth)acrylate or polyethylene glycol (meth)acrylate.

11. The method according to claim 5, wherein the amino group-containing unsaturated monomer includes (N,N)-dimethylaminoethyl(meth)acrylate or (N,N)-dimethylaminopropyl(meth)acrylamide, or a quaternary product thereof.

\* \* \* \* \*